United States Patent [19]
Wassermann

[11] Patent Number: 5,451,234
[45] Date of Patent: Sep. 19, 1995

[54] FRICTION FIT FASTENING APPARATUS AND METHOD

[76] Inventor: Paul Wassermann, Dipo. Eng. Ret. Hans Thoma Platz No. 10, 69121 Heidelberg, Germany

[21] Appl. No.: 966,918

[22] Filed: Oct. 27, 1992

[51] Int. Cl.$^6$ ............................................. A61B 17/132
[52] U.S. Cl. ................................................... 606/203
[58] Field of Search ................. 606/203, 201, 202; 24/301, 302, 300, 19

[56] References Cited

U.S. PATENT DOCUMENTS

| | | |
|---|---|---|
| 268,407 | 12/1882 | Hughes. |
| 1,252,260 | 1/1918 | Gilberg. |
| 3,156,243 | 11/1964 | Sculley. |
| 3,461,863 | 8/1969 | Sullinger. |
| 3,910,280 | 10/1975 | Talonn ............................. 606/203 |
| 4,727,885 | 3/1988 | Ruff ................................. 606/203 |
| 4,911,162 | 3/1990 | Wolff ............................... 606/203 |
| 5,084,062 | 1/1992 | Sturm .............................. 606/203 |

FOREIGN PATENT DOCUMENTS 2931 of 1892 United Kingdom ................ 606/203

Primary Examiner—Tamara L. Graysay
Attorney, Agent, or Firm—Kenyon & Kenyon

[57] ABSTRACT

A friction fit fastening device in which a stretchable elongated strap applies radial tension to a body limb or the like to restrict blood flow or to secure objects to the body. The strap can be pulled taut to a desired tension and than held with a fastener when the strap is returned to its natural state. The strap is prevented from slipping because of friction applied to the strap by the fastener. The strap can be easily adjusted or removed by pulling on the strap which decreases the friction applied to the strap by the fastener.

14 Claims, 10 Drawing Sheets

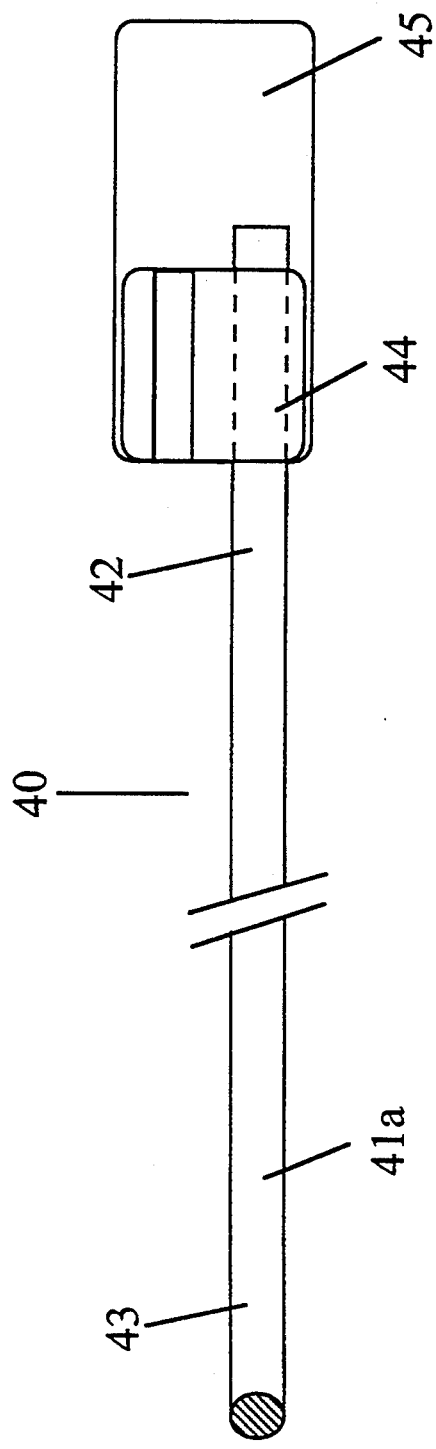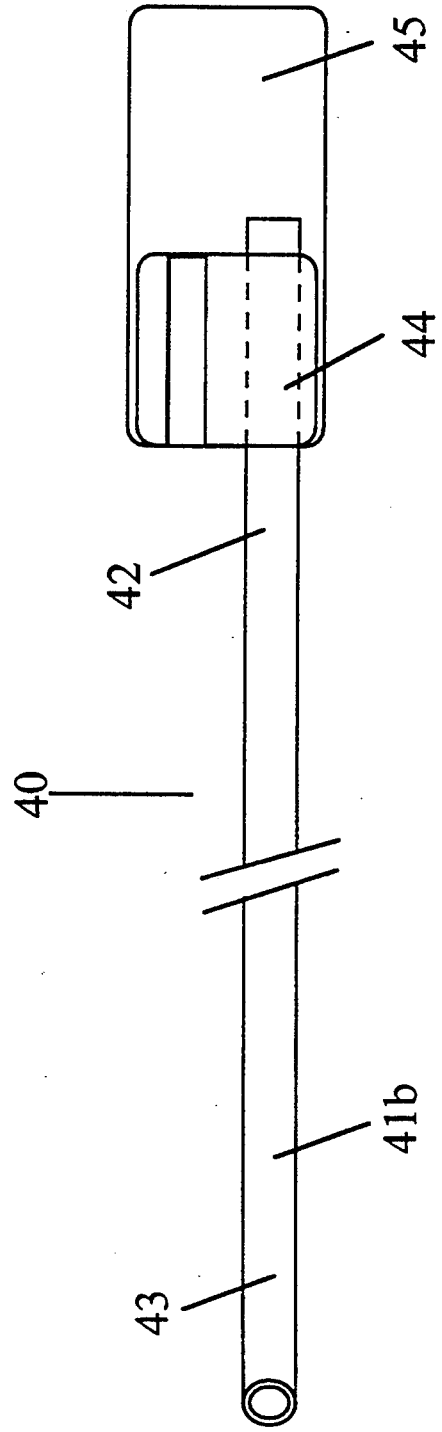

FRICTION FIT FASTENING APPARATUS AND METHOD

FIELD OF INVENTION

The present invention is directed to a friction fit apparatus and method. In particular, it relates to a system and apparatus and method that provides for the fastening of an elastic strap or tube using frictional engagement of a fastener with the strap or tube, and when employed as a tourniquet system, applies radial tension to body limbs and the like and can be applied, adjusted and removed easily and efficiently.

BACKGROUND OF THE INVENTION

It is often desirable to use flexible and elastic straps to fasten items to other items or to apply pressure against body limbs and the like. In the medical environment, these straps can be used as a tourniquet, surrounding, for example, a body limb, to restrict blood circulation by being pulled taut around the body limb and fastened. In the non-medical environment, these straps can be used to secure items to the body, surrounding the body or part thereof, such as an accessory belt to the waist of an underwater diver, or a knife or the like to the thigh of an underwater diver, or a timepiece or the like to a person's wrist, or as a fashion accessory, such as a belt.

In the medical environment, during certain medical procedures, it is often necessary to restrict blood circulation in a particular body limb or particular blood vessel of a patient to avoid excessive loss of blood.

For example, an injury or medical procedure may require that the blood circulation in a body limb be restricted for a period of time until the medical procedure is completed. In addition, it is often necessary to restrict blood circulation in a particular body limb when taking a sample of blood from a blood vessel. These procedures are often called Vena Procedures.

Tourniquet systems are often used to restrict blood circulation in patients by applying pressure to a body limb or blood vessel. Generally, tourniquet systems are made of elongated straps constructed of any one of various materials connected to fastening devices to keep the elongated strap taut against the limb or blood vessel.

Materials such as leather, rubber, elastic webbing and the like have been used for the elongated straps of a tourniquet system. Since these materials vary in elasticity, the effectiveness and comfort of tourniquet systems widely vary. Moreover, the width of the elongated straps as applied against the surface of a body limb often vary the effectiveness and comfort of the tourniquet system. For example, an elongated strap in the shape of a thin tube, although effective for restricting blood flow, can often cut into the surface of the body limb causing patient trauma. On the other hand, an elongated strap in the shape of a wide band may cause less patient trauma but may result in unwanted blood flow during the medical procedure.

Tourniquet fasteners are usually in the form of mechanical locks or mechanical metal buckles, where the elongated strap is inserted into a metal or plastic hoop, for example, and secured thereby. Other types of fasteners that have been used are hoop methods and lock methods, such as VELCRO, or the tying of the elongated strap in a knot. Many of these fasteners are expensive to produce and thus increase the cost of the tourniquet system and prohibit the possibility of a disposal tourniquet system. In addition, many of these fasteners involve several steps that must be performed by the attending physician to secure the elongated straps. This increases the time it may take to fasten the tourniquet system and restrict blood circulation, as well as the time it may take to adjust the tension of the tourniquet system or to restore blood circulation. Moreover, the possibility of a fastener malfunction or fastener jam generally increases with its complexity. Also, when the elongated strap is simply tied in a knot, there is a significant opportunity for pinching of the patient's skin to occur. On the other hand, many less complex fasteners may slip in practice resulting in unwanted blood circulation during a medical procedure. This can result in distraction of the attending physician who may be forced to delay his procedure.

Another problem associated with present tourniquet systems is that many fasteners pull the elongated strap away from the surface of the limb. This can often result in patient discomfort due to skin, body hair or muscle that can be pulled or caught in the gaps and contacts between the elongated straps and the fastener. This type of patient discomfort is often referred to as "pinching." Many tourniquet systems also have increased pressure points due to a portion of the fastener surface which is pressed against the surface of the body limb at an angle to the elongated strap. This can result in patient discomfort due to an increased pressure point on the limb and can also lead to hair, skin or muscle pulling.

In addition to medical uses, the friction fit fastening device of the present invention is also useful as a securing mechanism to secure items to the body. For example, many persons who underwater dive or snorkel secure equipment and gear, such as an accessory belt, to their body so as to allow easy movement of the body and limbs while keeping the equipment and gear in such a position to allow easy and quick access. These items are often attached to elongated straps constructed of any one of various materials. The elongated straps are connected to fastening devices and are placed around the waist, a body limb or the like and kept taught by the fastening device.

Similar to tourniquet designs, materials such as leather, rubber, elastic webbing and the like have been used for the elongated straps of the securing mechanism. Since these materials vary in elasticity, the effectiveness and comfort of the securing mechanism widely vary.

As with tourniquet designs, the fasteners of such securing mechanism are usually in the form of mechanical locks or mechanical metal buckles, where the elongated strap is inserted into a metal or plastic hoop, for example, and secured thereby. Other types of fasteners that have been used are hoop methods and lock methods, such as VELCRO, or the tying of the elongated strap in a knot. Many of these fasteners are expensive to produce and thus increase the cost of the securing mechanism. In addition, many of these fasteners involve several steps that must be performed by the user to secure the elongated straps. This increases the time it may take to fasten the securing mechanism as well as the time it may take to adjust the tension of the securing mechanism. Moreover, the possibility of a fastener malfunction or fastener jam generally increases with its complexity. Also, when the elongated strap is simply tied in a knot, there is a significant opportunity for pinching of the user's skin to occur.

Accordingly, it is an object of the present invention to provide a friction fit fastening system which employs frictional engagement of an elastic strap or tube in a fastener to secure items.

It is yet another object of the present invention to provide a friction fit fastening system which applies radial tension against a body limb or the like.

It is yet another object of the present invention to provide an inexpensive friction fit fastening apparatus and method.

It is another object of the present invention to provide a friction fit fastening apparatus and method which is effective in restricting blood circulation.

It is still another object of the present invention to provide a friction fit fastening apparatus and method which can be used easily and efficiently by attending medical personnel to restrict blood circulation.

It is another object of the present invention to provide a friction fit fastening apparatus and method which can be applied to a patient with little or no trauma.

It is still another object of the present invention to provide a friction fit fastening apparatus which may be disposable upon use.

SUMMARY OF THE INVENTION

In accordance with this invention, the foregoing objects are achieved primarily by using a stretchable elongated strap that can be pulled taut in a radial position around a body limb or similar object. The elongated strap can be held in this position by a fastener employing friction against the strap so as to eliminate slippage of the elongated strap in the fastener.

More particularly, the friction fit fastening device of the present invention consists of a stretchable elongated strap, and a fastener. The stretchable elongated strap can have various cross-sectional shapes, such as a round, oval or rectangular cross-sectional shape. The stretchable elongated strap has a first end and a second end, the first end of the strap is connected to the fastener and the second end is to be used to frictionally engage the fastener. The stretchable elongated strap has substantially fixed circumferential surface dimensions in its un-stretched state at least at the second end. The fastener has at least one cavity, the cavity is arranged to accept and frictionally engage the stretchable elongated strap therein. The cavity comprises at least one longitudinal channel to accept the stretchable elongated strap in its stretched state, and is arranged to grasp the stretchable elongated strap holding it securely in the cavity.

The cavity and longitudinal channel can receive the stretchable elongated strap by temporarily decreasing the circumferential surface dimensions of the strap. The circumferential surface dimensions of the stretchable elongated strap can be temporarily decreased by the user, or someone assisting the user, by pulling on the strap to stretch it or by squeezing the stretchable elongated strap into a V-shape or a reverse V-shape near the fastener. After placing the stretchable elongated strap through the longitudinal channel into the cavity on the fastener and ceasing the temporary stretching, the elasticity or retroactive factor of the strap causes the strap to attempt to return to its natural, un-stretched state. This increases the circumferential surface dimensions of the stretchable elongated strap and increases the friction against the walls of the cavity in the fastener, which prevents the strap from slipping. The stretchable elongated strap may then be placed in a radial position around a body limb or the like and secured in the fastener.

To adjust the radial tension of the stretchable elongated strap around the body limb or the like, the user can pull the strap, thus stretching the strap and decreasing its circumferential surface dimensions. This decreases the friction of the strap against the cavity walls and allows the strap to move in the longitudinal channel of the fastener.

To release the stretchable elongated strap from the fastener, the strap can be pulled to decrease its circumferential surface dimensions and then pulled out of the longitudinal channel and cavity in the fastener. This process can be accomplished by pulling the stretchable elongated strap in a direction away from the body limb, which stretches the strap and pulls the strap out of the longitudinal channel in the fastener. To facilitate the removal of the stretchable elongated strap from the longitudinal channel in the fastener, the stretchable elongated strap can also be squeezed near the fastener causing the strap to form a reverse V-shape.

BRIEF DESCRIPTION OF THE DRAWINGS

FIG. 8 is a top-view diagrammatic illustration of the stretchable elongated tube friction fit fastening apparatus in accordance with the present invention;

FIG. 8A is a top view diagrammatic illustration of the stretchable elongated tube friction fit fastening apparatus in accordance with the present invention employing a solid schematically show stretchable elongated tube;

FIG. 8B is a top view diagrammatic illustration of the stretchable elongated tube friction fit fastening apparatus in accordance with the present invention employing a schematically shown oval shaped stretchable elongated tube;

DETAILED DESCRIPTION

Figure 1:
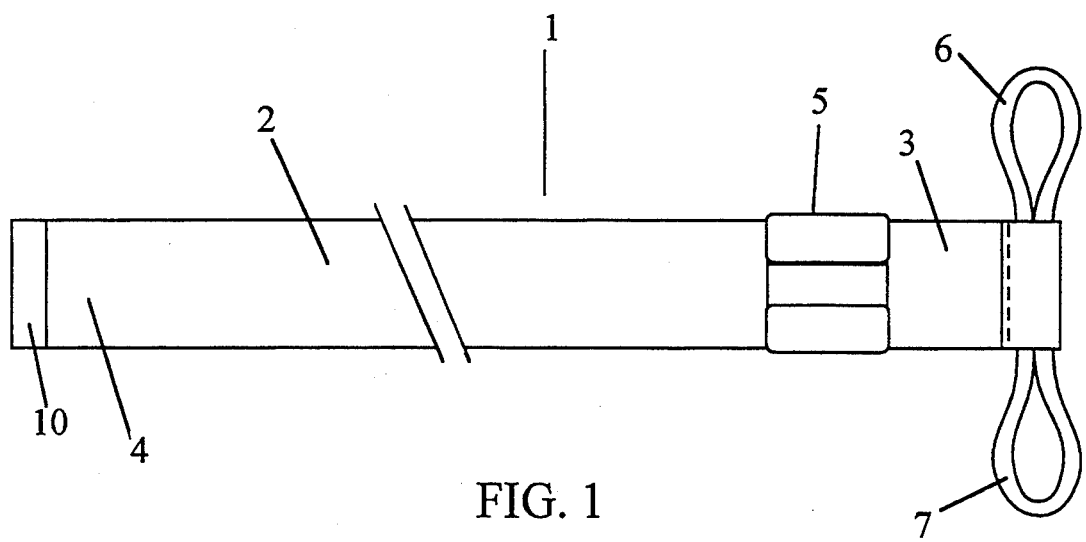
FIG. 1 is a top-view diagrammatic illustration of the stretchable elongated band friction fit fastening apparatus employing finger-cord loops in accordance with the present invention.

Referring now to the drawings, and initially FIG. 1, there is illustrated a top-view of a stretchable elongated band friction fit fastening apparatus, indicated generally at 1, in accordance with the present invention. A stretchable elongated band 2 is illustrated and has a proximal end, indicated generally at 3, and a distal end, indicated generally at 4. A fastener 5 is secured to the stretched elongated band 2 at or near the proximal end 3 of the band 2. The stretchable elongated band 2 can be placed radially around a body limb or the like and pulled taut. The distal end 4 of the stretchable elongated band 2 can then be frictionally engaged by the fastener 5. The fastener 5 grasps the distal end 4 of the stretchable elongated band 2 using friction, as described in more detail below, and prevents the distal end 4 of the stretchable elongated band 2 from slipping in the fastener 5. Accordingly, the stretchable elongated band friction fit fastening apparatus 1 is adapted to apply pressure to a body limb or the like. In one aspect of the invention, the stretchable elongated band friction fit fastening device 1 is adapted like a tourniquet to apply pressure to a body limb to restrict blood flow.

The stretchable elongated band 2 can be constructed of any stretchable materials, such as natural rubber, synthetic rubber, or the like, polyurethane, latex, elastic webbing, elastic tape, natural or synthetic rubber coated or braided with natural fibers, such as cotton, or coated with synthetic fibers, such as nylon, polyester, acrylic or polyurethane, or coated or braided with similar materials. The elastic webbing or tape can be made of a weaved fabric consisting natural or synthetic fibers or thread weaved with natural or synthetic rubber threads.

The stretchable elongated band 2 can be made of different sizes and materials, leading to different stretch coefficients. The term "stretch coefficient" is intended to denote the increase in the percentage of the length of the stretchable elongated band 2 in its un-stretched state as compared to its stretched state. For example, a stretchable elongated band 2 having a length of 100 millimeters in its un-stretched state that can be stretched to 150 millimeters in its stretched state has a stretch coefficient of 50 percent. Generally, for tourniquets systems used in accordance with the present invention, a stretch coefficient of between 30 and 50 percent is usually effective. Experiments have shown that for tourniquet systems, a stretch coefficient of between 37 and 42 percent is preferred. Moreover, for tourniquets used in Vena Procedures, a stretchable elongated band 2 having the following dimensions is generally effective: width of about 20 millimeters to 30 millimeters and a thickness of about 1.0 millimeters to 2.5 millimeters. Experiments have shown that for tourniquet systems, a stretchable elongated band 2 with a width of about 25 millimeters and a thickness of between 1.5 to 2.0 millimeters is preferred. Although the length of the stretchable elongated band 2 will be dependent on the size of the particular body limb that the tourniquet will be used on, a length of about 300 millimeters to 450 millimeters is effective for many procedures. These figures are for illustrative purposes only and it can readily be seen by those skilled in the art that the dimensions of the stretchable elongated band 2 and the materials used to construct it can be widely varied.

The fastener 5 can be constructed of any rigid material, such as plastic or metal, for example: nylon, acrylic, polyester, acetal, stainless steel, brass, aluminum, aluminum alloy, delrin, polysulfone or the like. The stretchable elongated band 2 or the fastener 5 when used for tourniquet systems could be constructed of materials that are easily sterilized so that either, or both, could be re-used on other persons or patients. On the other hand, the stretchable elongated band 2 or the fastener 5 could be made out of a less expensive material which may allow either of them to be efficiently disposed of after a single use.

Figure 2:
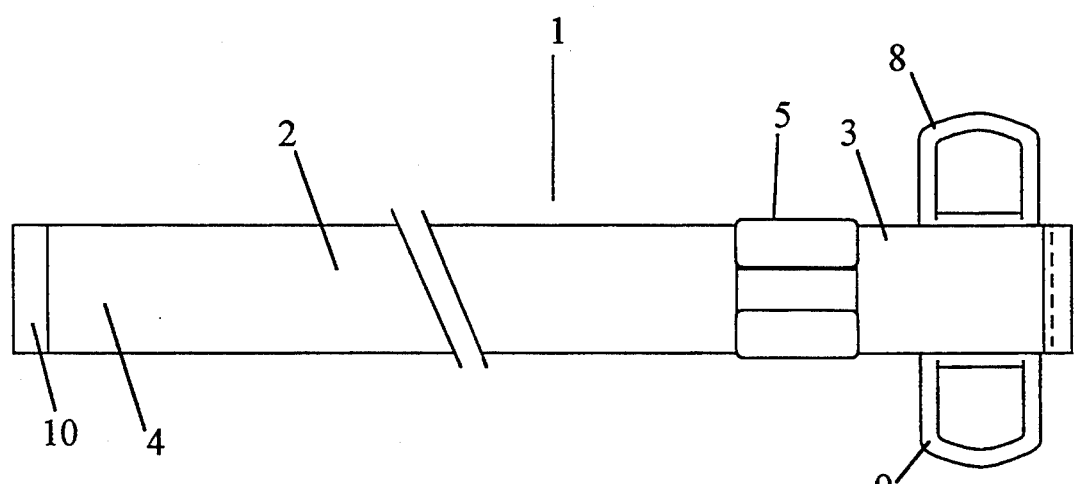
FIG. 2 is a top-view diagrammatic illustration of the stretchable elongated band friction fit fastening apparatus employing D-ring loops in accordance with the present invention.

Finger-cord loops 6 and 7 may be located at the proximal end 3 of the stretchable elongated band 2 and are used to assist the user in gripping the proximal end 3 of the stretchable elongated band 2 so that the distal end 4 of the stretchable elongated band 2 can be pulled taut while placed around a body limb or the like. The finger-cord loops 6 and 7 also assist the user in holding the fastener 5 in place against the body limb or the like while the friction fit apparatus is being applied to the body limb or the like. The finger-cord loops 6 and 7 could be replaced with any suitable object, or the width of the proximal end 3 of the stretchable elongated band 2 can be increased. Increasing the width of the band 2 at its proximal end 3 allows it to be easily grasped and handled. The finger cord-loops 6 and 7 could also be replaced with "D" shaped rings, attached to the proximal end 3 of the stretchable elongated band 2. For example, FIG. 2 shows a top-view of the stretchable elongated band friction fit fastening apparatus 1 employing "D" shaped rings 8 and 9, in accordance with the present invention. Moreover, it would be practical to attach a "D" shaped gripping device to each edge of the proximal end 3 of the stretchable elongated band 2 in a hinged fashion so that the "D" shaped rings 8 and 9 could be turned away from the body limb or the like for better grip.

It is also possible to connect the "D" shaped gripping devices 8 and 9, or other gripping devices, directly to the fastener 5 rather than to the proximal end 3 of the stretchable elongated band 2 to make the fastener 5 easier to grip. Although the finger cord-loops 6 and 7, "D" shaped gripping devices 8 and 9, widening of the stretchable elongated band 2 at its proximal end 3, or the like, make the friction fit fastening device of the present invention easier to use, no such gripping devices are necessary to use the friction fit fastening device of the present invention. In fact, the user can grasp the fastener 5 while pulling the stretchable elongated band 2 around a body limb or the like.

Figure 3:
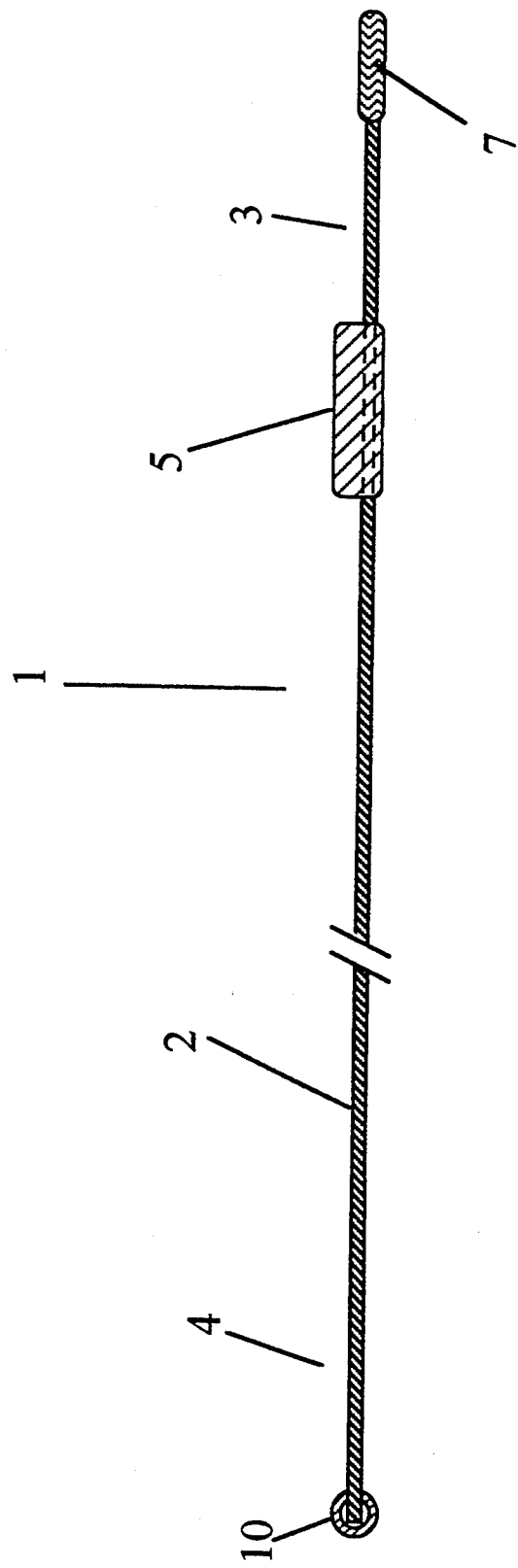
FIG. 3 is a side-view diagrammatic illustration of the stretchable elongated band friction fit fastening apparatus employing finger-cord loops in accordance with the present invention.

FIG. 3 shows the side-view of the stretchable elongated band tourniquet system 1 employing finger-cord loops 6 and 7 in accordance with the present invention. At the distal end 4 of the stretchable elongated band 2 is shown a stiff plastic material 10, which may be in a tubular shape and which may be opened on one side to accept the distal end 4 of the stretchable elongated band 2. The stiff plastic material or tube 10 may be attached to the stretchable elongated band 2 with adhesive or the like, or it may also be sewn to the stretchable elongated band 2. The plastic material or tube 10 is used to assist the user in grasping the distal end 4 of the stretchable band 2 so that it can be pulled taut around a body limb. As with the finger cord-loops 6 and 7, the plastic material or tube 10 may be replaced with any suitable gripping device. In the alternative, the friction fit fastening apparatus 1 of the present invention can be used without any gripping device attached to the distal end 4 of the stretchable elongated band 2.

Figure 4:
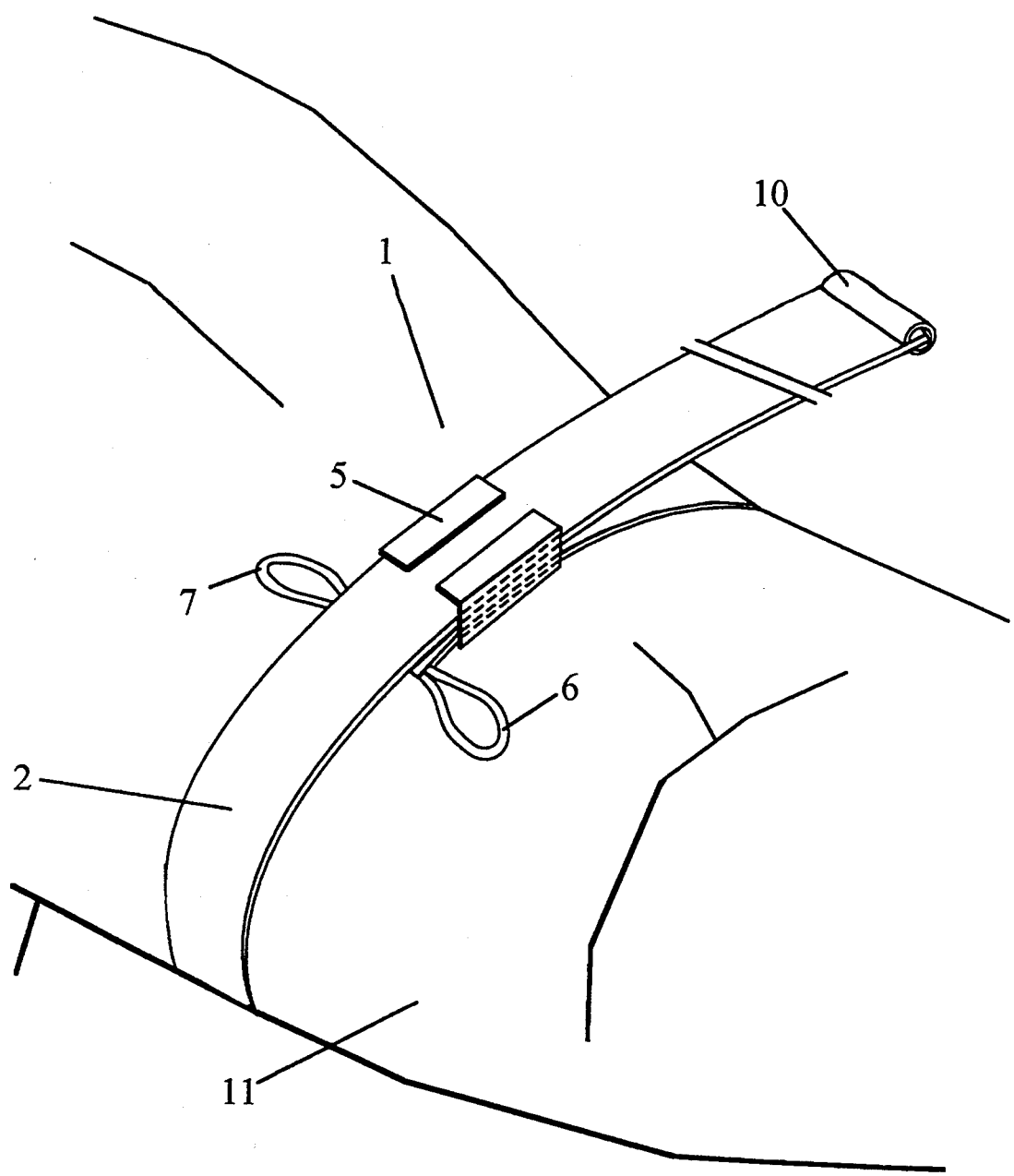
FIG. 4 is a diagrammatic illustration of the stretchable elongated band friction fit fastening apparatus employing finger-cord loops placed around a body limb in accordance with the present invention.

In practice, one aspect of the stretchable elongated band type of the friction fit fastening device 1 of the present invention is adapted to be placed around a body limb to restrict the flow of blood. Referring to FIG. 4, the stretchable elongated band friction fit fastening device 1 of the present invention is illustrated placed around a body limb 11.

Figure 5:
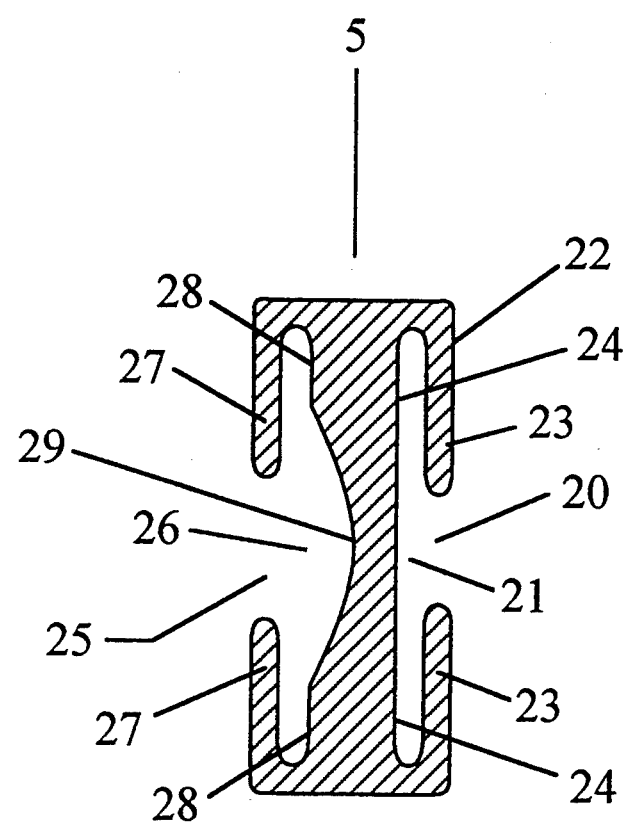
FIG. 5 is a cross-sectional illustration of the stretchable elongated band fastener of the friction fit fastening apparatus in accordance with the present invention.
Figure 6:
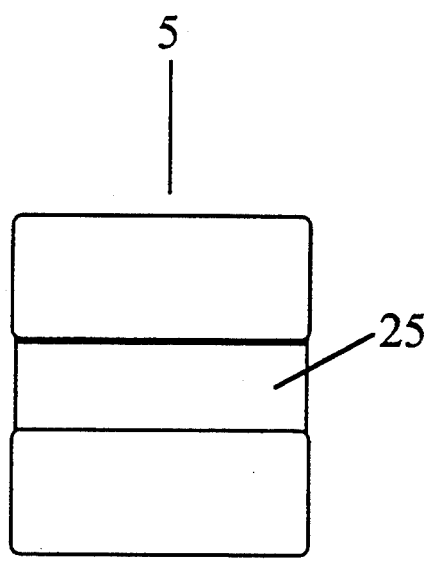
FIG. 6 is a top-view diagrammatic illustration of the stretchable elongated band fastener in accordance with the present invention.
Figure 7:
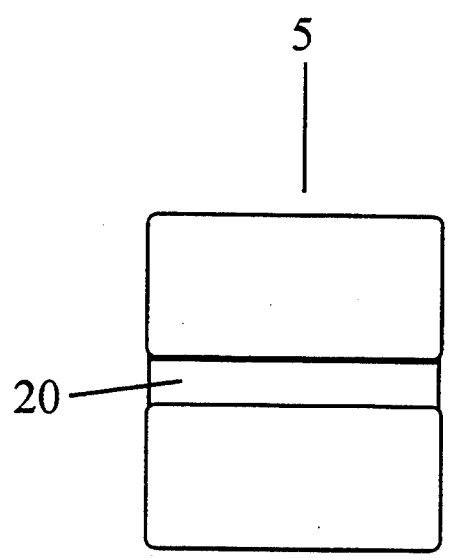
FIG. 7 is a bottom-view diagrammatic illustration of the stretchable elongated band fastener in accordance with the present invention.

The stretchable elongated band fastener 5 of the present invention is further illustrated in FIGS. 5, 6 and 7. In FIG. 5, a cross-sectional view of the fastener 5 is shown. A lower opening 20 in the fastener 5 is arranged to place the proximal end 3 of the stretchable elongated band 2 into and out of a lower cavity 21, the lower cavity 21 forming a lower longitudinal channel in fastener 5. The width of the lower longitudinal channel should be substantially the same or slightly greater than the width of the proximal end of the stretchable elongated band. The lower surface of the fastener, indicated generally at 22, would be placed near or against the body surface during the friction fit fastening device's application on a body limb 11.

Lower arms, indicated at 23, and lower walls, indicated at 24, are for applying friction against the proximal end 3 of the stretchable elongated band 2 to prevent slippage during the friction fit fastening device's application. The distance between the lower arms 23 and the lower walls 24 (channel depth) can be slightly less than the thickness of the proximal end 3 of the stretchable elongated band 2. The proximal end 3 of the stretchable elongated band 2 can be placed in the lower longitudinal channel of the lower cavity 21 between the lower arms 23 and lower walls 24 through the lower opening 20. By stretching the stretchable elongated band 2, the circumferential surface dimensions of the stretchable elongated band 2 decrease. Thus, it becomes easier to fit the stretchable elongated band 2 through the lower opening 20 into the lower longitudinal channel of the lower cavity 21. To facilitate the entry of the stretchable elongated band 2 into the lower opening 20 in the fastener device 5, the band 2 can be squeezed near the fastener device 5 causing the band 2 to form a V-shape or a reverse V-shape. Moreover, since the circumferential surface dimensions of the stretchable elongated band 2 are decreased during stretching, the thickness of the band 2 is decreased during stretching. Since the thickness of the stretchable elongated band 2 is temporarily decreased, the friction applied to the band 2 by the lower arms 23 and lower walls 24 is decreased. The stretchable elongated band 2 can thus be easily manipulated into lower cavity 21 between the lower arms 23 and the lower walls 24. As soon as the user stops stretching the stretchable elongated band 2, the elasticity or retroactive factor of the band 2 forces the band 2 to attempt to return to its natural shape, thereby increasing its circumferential surface dimensions. The thickness of the stretchable elongated band 2 increases and the friction applied to the band by the lower arms 23 and lower walls 24 increases. This increased friction anchors the stretchable elongated band 2 to the fastener device 5 and keeps the band 2 from slipping during the friction fit fastening device's application.

Although it is generally not necessary to remove or manipulate the proximal end 3 of the stretchable elongated band 2 from the fastener 5, this aspect of the present invention allows the stretchable elongated band 2 to be easily replaced should it become worn or damaged. In addition, this aspect of the present invention makes it possible to have disposal stretchable elongated bands 2, while retaining the fastener 5 for future use. This is particularly useful for tourniquet systems which often require sterilization or disposal after use due to blood contamination or other contamination. It may also lower the cost of the friction fit fastening device.

In yet another implementation of the invention, the stretchable elongated band friction fit fastening device 1 can have the proximal end 3 of the stretchable elongated band 2 permanently attached to the fastener 5. Thus, the stretchable elongated band 2 can be attached to the surface of the fastener 5, or, the band 2 can be placed into the lower cavity 21 and then attached to the fastener 5 with adhesive or the like.

After the proximal end 3 of the stretchable elongated band 2 is placed into the lower cavity 21, the user can place the friction fit fastening apparatus 1 around a body limb 11. The lower surface 22 of the fastener 5 would be placed near or against the body surface and the stretchable elongated band 2 would be placed radially around the body limb 11.

An upper opening 25 in the fastener 5 is illustrated and is for placing the distal end 4 of the stretchable elongated band 2 into and out of an upper cavity 26, the upper cavity 26 forming an upper longitudinal channel in the fastener device 5. The width of the upper longitudinal channel should be substantially the same or slightly greater than the width of the distal end of the stretchable elongated band 2. Upper arms 27 and upper walls 28 are illustrated and are for applying friction against the distal end 4 of the stretchable elongated band 2 to prevent slippage during the friction fit fastening device's application. The distance between the upper arms 27 and the upper walls 28 (channel depth) is slightly less than the thickness of the distal end 4 of the stretchable elongated band 2 in its un-stretched state. After the stretchable elongated band 2 has been placed around the body limb 11, the distal end 4 of the stretchable elongated band 2 can be placed in the upper longitudinal channel of the upper cavity 26 between the upper arms 27 and the upper walls 28 through the upper opening 25. By stretching the stretchable elongated band 2, the circumferential surface dimensions of the stretchable elongated band 2 decrease. Thus, it becomes easier to fit the distal end 4 of the stretchable elongated band 2 through the upper opening 25 into the upper longitudinal channel of the upper cavity 26 between the upper arms 27 and the upper walls 28. To facilitate the entry of the stretchable elongated band 2 through the upper opening 25 into the upper cavity 26, the band 2 can be squeezed near the fastener 5 causing the band 2 to form a V-shape or a reverse V-shape. Moreover, since the circumferential surface dimensions of the distal end 4 of the stretchable elongated band 2 are decreased during stretching, the thickness of the distal end 4 of the stretchable elongated band 2 is decreased during stretching. Since the thickness of the distal end 4 of the stretchable elongated band 2 is temporarily decreased, the friction applied to the distal end 4 of the band 2 by the upper arms 27 and upper walls 28 is decreased. The distal end 4 of the stretchable elongated band 2 can thus be easily manipulated into upper cavity 26 between the upper arms 27 and the upper walls 28. As soon as the user stops stretching the stretchable elongated band 2, the elasticity or retroactive factor of the band 2 forces the band 2 to attempt to return to its natural shape, thereby increasing its circumferential surface dimensions. The thickness of the distal end 4 of the stretchable elongated band 2 increases and the friction applied to the distal end 4 of the band 2 by the upper arms 23 and upper walls 24 increases. This increased friction anchors the distal end 4 of the stretchable elongated band 2 to the fastener 5 and keeps the band 2 from slipping during the friction fit fastening device's application.

The concave portion 29 of the upper cavity 26 of the fastener 5 is illustrated and allows the distal end 4 of the stretchable elongated band 2 to be more easily manipulated in and out of the upper cavity 26. It provides additional space in the upper cavity 26 and helps guide the stretchable elongated band 2 into and out of the upper longitudinal channel of the upper cavity 26, between the upper arms 23 and the upper walls 24. It is possible, however, to use the friction fit fastening device 1 of the present invention without implementing the concave portion 29 of the fastener 5.

In FIG. 6, a top-view of the fastener 5 is shown. The upper opening 25 is partially illustrated and traverses the upper surface of the fastener 5. In FIG. 7, a bottom-view of the fastener 5 is shown. The lower opening 20 is partially illustrated and traverses the bottom surface of the fastener 5.

Once the friction fit fastening apparatus 1 is applied to a body limb 11 of a person as indicated in FIG. 4, the user can adjust the radial tension applied to the limb by the stretchable elongated band 2 by pulling on the distal end 4 of the stretchable elongated band 2. This will stretch the stretchable elongated band 2, decreasing its circumferential surface dimensions and lessening the friction applied to the distal end 4 of the stretchable elongated band 2 by the upper arms 27 and upper walls 28. This will allow the stretchable elongated band 2 to slip in the fastener 5 until the desired radial tension is achieved. Once the desired radial tension is achieved, the user need only stop pulling on the distal end 4 of the stretchable elongated band 2. The friction fit fastening device 1 will retain this desired radial tension because the elasticity or retroactive factor of the stretchable elongated band 2 will force the band 2 to attempt to return to its natural circumferential surface dimensions. This increases the friction against the distal end 4 of the stretchable elongated band 2 applied by the upper arms 27 and the upper walls 28 and will anchor the stretchable elongated band 2 in the fastener 5.

To release and remove the friction fit fastening apparatus 1 from the person, the user can pull on the distal end 4 of the stretchable elongated band 2 in a direction away from the body surface 11. This will stretch the stretchable elongated band 2 and allow it to escape from the fastener 5 through the upper opening 25. In addition, the user can squeeze the edges of the stretchable elongated band 2 near the upper opening 25 causing the band 2 to form a reverse V-shape to expedite its removal through the opening 25.

In another implementation of the present invention, the stretchable elongated band 2 can be round or tubular in shape. Referring to FIG. 8, there is illustrated a top-view of a stretchable elongated tube friction fit fastening apparatus, indicated generally at 40, in accordance with the present invention. A stretchable elongated tube 41 is illustrated and has a proximal end, indicated generally at 42, and a distal end, indicated generally at 43. The proximal end 42 of the stretchable elongated tube 41 is anchored to a fastener 44. The stretchable elongated tube 41 can be placed radially around a body a limb or the like and pulled taut. The distal end 43 of the stretchable elongated tube 41 can then be anchored to the fastener 44. The fastener 44 frictionally engages the distal end 43 of the stretchable elongated tube 41 using friction and prevents the distal end 43 of the stretchable elongated tube 41 from slipping in the fastener 44. According to one aspect of the present invention, the stretchable elongated tube friction fit fastening apparatus 40 can be adapted like a tourniquet to apply pressure to a body limb to restrict blood flow.

The stretchable elongated tube 41 can be made of natural rubber, synthetic rubber, plastic, braided or woven elastic, elastic tape, polyvinyl chloride, polyurethane, silicon, or the like, and may be coated with natural or synthetic rubber, plastic, or coated with natural fibers, such as cotton, or coated with synthetic fibers, such as nylon, polyester, polypropylene or polyurethane, or coated with similar materials. The stretchable elongated tube 41 can have a circular, oval, square, or similar cross-sectional shape. In addition, the stretchable elongated tube 41 can be hollow or solid. For example, a solid stretchable elongated tube is illustrated schematically in FIG. 8A as reference numeral 41a, and a stretchable elongated tube in the shape of an oval is illustrated schematically in FIG. 8B as reference numeral 41b.

The fastener 44 can be constructed of any rigid material, such as plastic or metal, for example: nylon, acrylic, polyester, acetal, stainless steel, brass, aluminum, aluminum alloy, delrin, polysulfone or the like. The fastener 44 can be attached to a flexible apron 45. The flexible apron 45 can be constructed of any flexible material such as cloth, felt, rubber, or the like. The flexible apron 45 disperses the tension of the stretchable elongated tube 41 after it has been pulled taut against a body limb. This helps the radial tension of the stretchable elongated tube 41 remain relatively consistent at all body contact points. This reduces trauma and reduces the risk of discomfort due to body hair, skin or muscle that can be pulled or caught in the gaps and contacts between the stretchable elongated tube 41 and the fastener 44.

Figure 9:
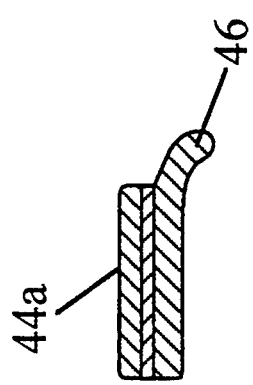
FIG. 9 is a side-view diagrammatic illustration of the stretchable elongated tube rib-shape fastener in accordance with the present invention.
Figure 10:
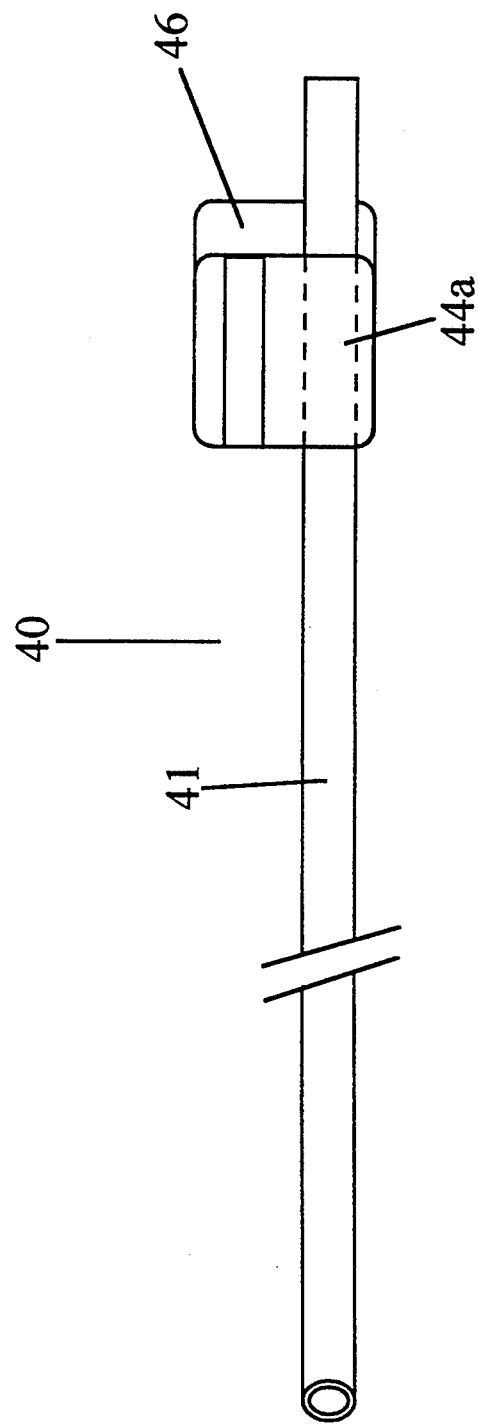
FIG. 10 is a top-view diagrammatic illustration of a stretchable elongated tube friction fit fastening apparatus employing a rib-shape fastener in accordance with the present invention.

As an alternative to the flexible apron 45, the fastener 44 can be constructed using a rib-shape design. Referring to FIG. 9, there is illustrated a side-view of a fastener 44a of a stretchable elongated tube friction fit fastening device, employing a rib-shape extension illustrated generally at 46. This rib-shape extension 46 is designed so that an extruded rounded edge is placed against the body limb during the friction fit fastening device's application. This design diminishes discomfort, or the "pinching" sensation, by decreasing the likelihood of skin, body hair or muscle being pulled or caught in the gaps and contacts between the stretchable elongated tube 41 and the fastener 44a. Referring to FIG. 10, there is illustrated a top-view of a stretchable elongated tube friction fit fastening device, indicated generally at 40, employing a rib-shape fastener 44a in accordance with the present invention.

The stretchable elongated tube 41, the fastener 44 or the flexible apron 45 can be constructed of materials that are easily sterilized so that any one of them, or all of them, can be re-used on other persons or patients. On the other hand, the stretchable elongated tube 41, the fastener 44 or the flexible apron 45 can be constructed of a less expensive material which may allow any of them, or all of them, to be efficiently disposed of after a single use. This is particularly useful for tourniquet systems which often require sterilization or disposal after use due to blood contamination or other contamination. It may also lower the cost of the friction fit fastening device.

Figure 11:
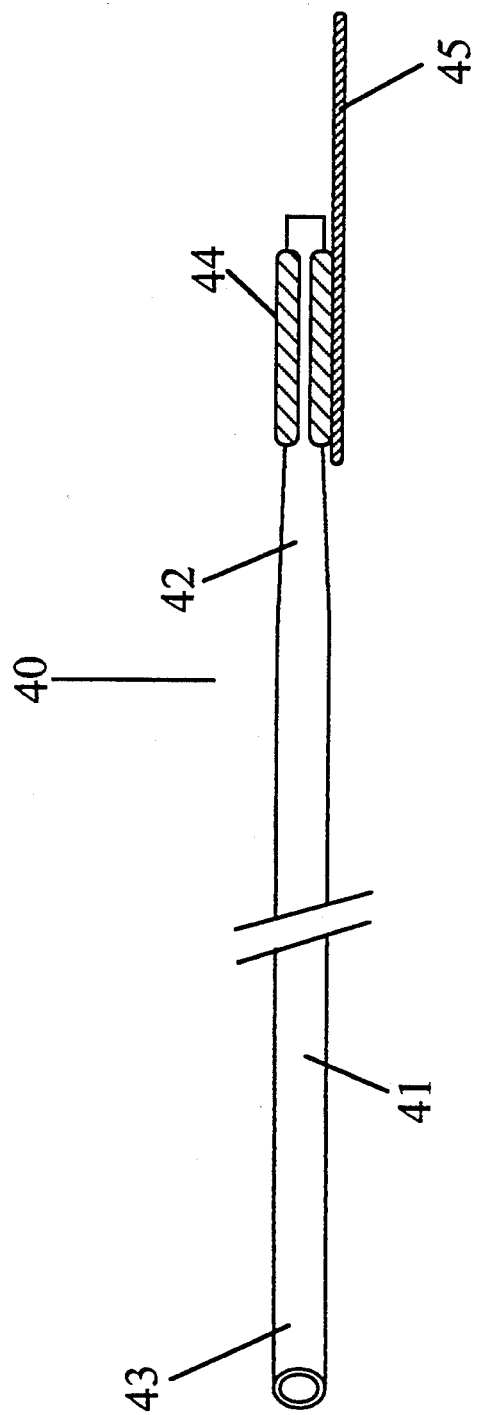
FIG. 11 is a side-view diagrammatic illustration of the stretchable elongated tube friction fit fastening apparatus in accordance with the present invention.
Figure 12:
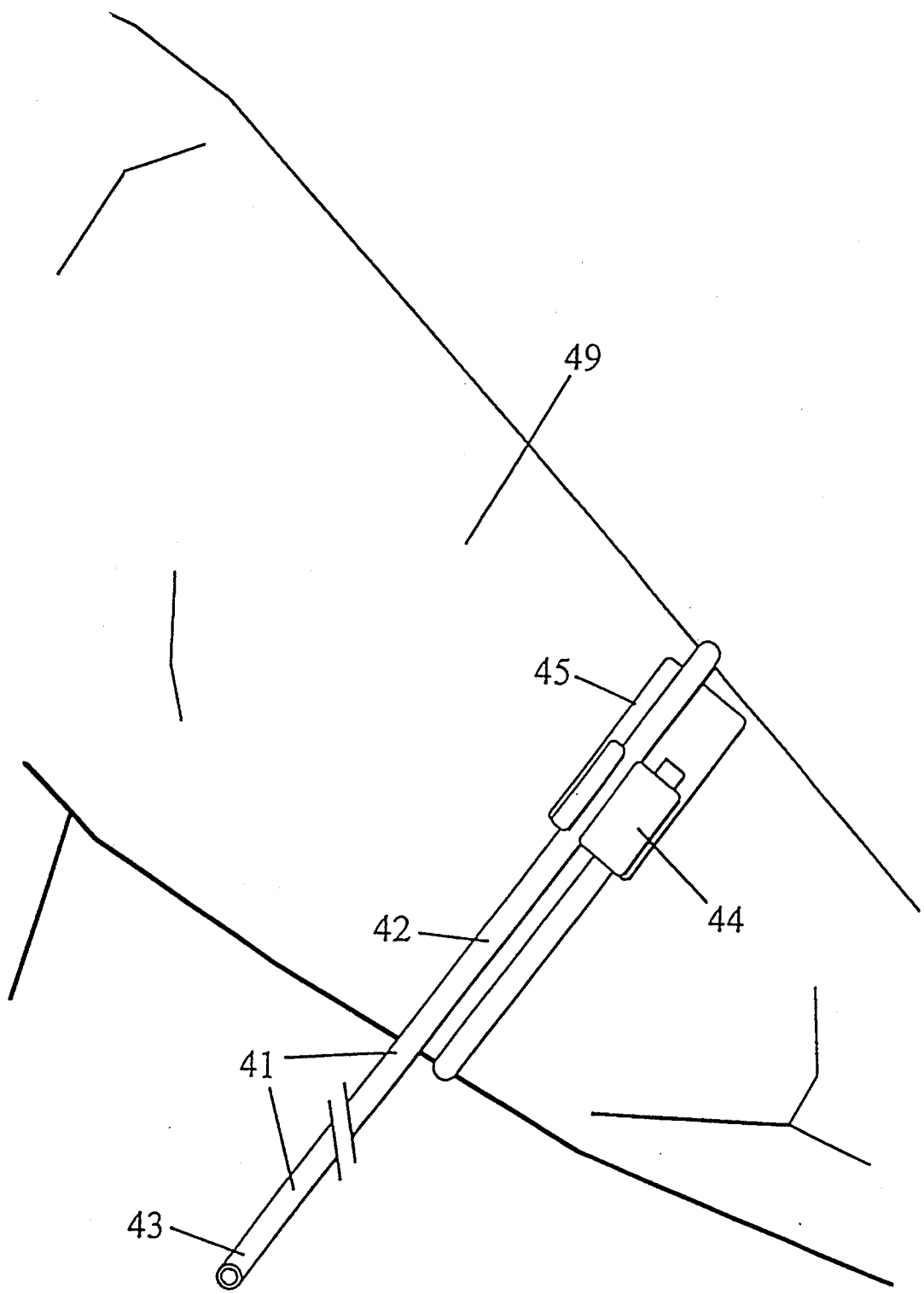
FIG. 12 is a diagrammatic illustration of the stretchable elongated tube friction fit fastening apparatus around a body limb in accordance with the present invention.

Referring to FIG. 11, a side-view of the stretchable elongated tube friction fit fastening apparatus 40 is illustrated. In practice, the stretchable elongated tube friction fit fastening apparatus 40 can be adapted as a tourniquet to be placed in a radial position around a body limb to restrict the flow of blood. Referring to FIG. 12, the stretchable elongated tube tourniquet system 40 is illustrated placed around a body limb 49.

Figure 13:
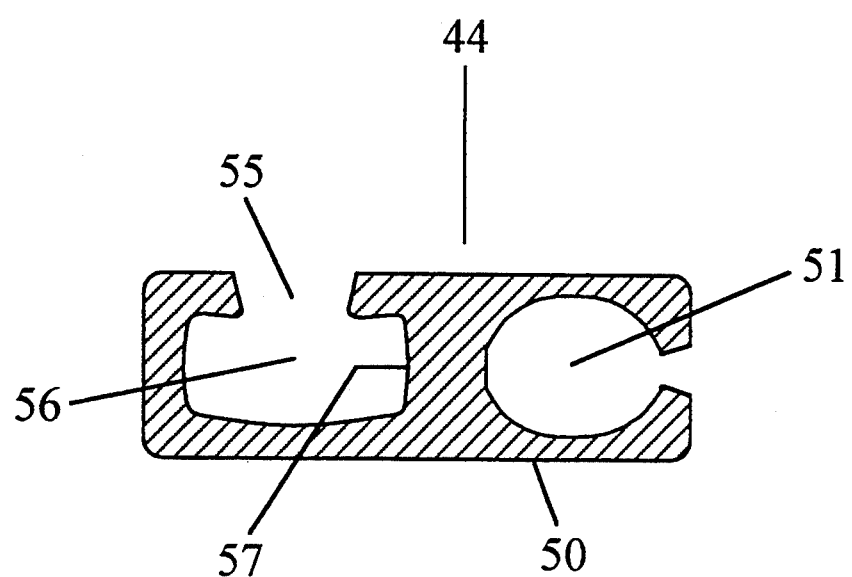
FIG. 13 is a cross-sectional illustration of the stretchable elongated tube fastener in accordance with the present invention.

FIG. 13 illustrates a cross-sectional view of the fastener 44. A lower surface 50 of the fastener 44 can be placed near or against the body surface, or it can be attached to the flexible apron 45. The proximal end 42 of the stretchable elongated tube 41 can be placed in a first cavity 51. The proximal end 42 of the stretchable elongated tube 41 may also be anchored in the first cavity 51 with adhesion or the like or may be otherwise suitably affixed to the fastener 44.

After the proximal end 42 of the stretchable elongated tube 41 is anchored to the fastener 44, the user can place the stretchable elongated tube friction fit fastening apparatus 40 on the body limb 49 of a person or patient. The user can place the flexible apron 45 on the body limb 49 and then place the stretchable elongated tube 41 radially around the body limb 49.

An opening 55 is for placing the distal end 43 of the stretchable elongated tube 41 into and out of a second cavity 56. The width of the opening 55 should be less than the diameter of the stretchable elongated tube 41 when the tube 41 is in the un-stretched state. Generally, the second cavity 56 has inner walls, indicated at 57, for grasping the distal end 43 of the tube 41. The inner walls 57 of the second cavity 56, are for applying friction against the stretchable elongated tube 41 to prevent slippage during the friction fit fastening device's application. The inner surface dimensions of the second cavity, defined by the inner walls 57 should be slightly less than the outer surface circumference of the stretchable elongated tube 41 when the tube 41 is in the un-stretched state.

After the stretchable elongated tube 41 has been placed around the body limb 49, the tube 41 can be placed in the second cavity 56 through the opening 55. By stretching the stretchable elongated tube 41, the circumferential surface dimensions of the tube 41 decrease. Thus, it becomes easier to fit the stretchable elongated tube 41 through the opening 55 into the second cavity 56. Moreover, since the circumferential surface dimensions of the stretchable elongated tube 41 are decreased during stretching, the friction applied to the tube 41 by the inner walls 57 of the second cavity 56 is decreased. The distal end 43 of the stretchable elongated tube 41 can thus be easily manipulated into second cavity 56. As soon as the user stops stretching the stretchable elongated tube 41, the elasticity or retroactive factor of the tube 41 forces the tube 41 to attempt to return to its natural shape, thereby increasing its circumferential surface dimensions. This increases the friction applied against the stretchable elongated tube 41 by the inner walls 57 of the second cavity 56 and anchors the tube 41 to the fastener 44 by stopping the tube 41 from slipping during the friction fit fastening device's application.

Once the stretchable elongated tube friction fit fastening apparatus 40 is applied to the body limb 49 of a person or patient as indicated in FIG. 11, the user can adjust the radial tension applied to the person's limb by the stretchable elongated tube 41 by pulling on the distal end 43 of the tube 41. This will stretch the stretchable elongated tube 41, decreasing its circumferential surface dimensions and decreasing the friction applied to the tube 41 by the inner walls 57 of the second cavity 56. This will allow the stretchable elongated tube 41 to slip in the fastener 44 until the desired radial tension is achieved. Once the desired tension is achieved, the user need only stop pulling on the distal end 43 of the stretchable elongated tube 41. The stretchable elongated tube 41 will retain this desired radial tension because the tube 41 will attempt to return to its natural dimensions, thus increasing the friction against the tube 41 applied by the inner walls 57 of the second cavity 56. This will stop the stretchable elongated tube 41 from slipping in the fastener 44.

To release and remove the friction fit fastening device from the person or patient, the user can pull on the distal end 43 of the stretchable elongated tube 41 in a direction away from the body surface. This will stretch the stretchable elongated tube 41 and allow it to escape from the fastener 44 through the opening 55. In addition, the user can squeeze the edges of the stretchable elongated tube 41 near the opening 55 to expedite its removal through the opening 55. This will flatten the stretchable elongated tube 41 allowing it to be easily removed through the opening 55.

Although FIG. 13 depicts the shape of the first cavity 51 and the second cavity 56 as relatively rectangular, other implementations of the present invention could include circular or oval cavity shapes. In addition, the proximal end 42 of the stretchable elongated tube 41 need not be placed in the first cavity 51. It could be attached directly to the surface of the fastener 44 or attached directly to the surface of the flexible apron 45. Moreover, the fastener 44 could be designed so that it has two cavities and openings similar to the second cavity 56 and the opening 55. In this implementation, the proximal end 42 of the stretchable elongated tube 41 could be removed easily from the fastener 44. This would facilitate the replacement of the stretchable elongated tube 41 without the need to replace the fastener 44.

Having thus described an exemplary embodiment of the invention, it will be apparent that various alterations, modifications and improvements will readily occur to those skilled in the art. Such obvious alterations, modifications and improvements, though not expressly described above, are nonetheless intended to be implied and are within the spirit and scope of the invention. Accordingly, the foregoing discussion is intended to be illustrative only, and not limiting; the invention is limited and defined only by the following claims and equivalents thereto.

What is claimed is:

1. A friction fit fastening apparatus comprising:
   a stretchable elongated band having a proximal end and a distal end, said stretchable elongated band having a predetermined first width and a predetermined first thickness in its un-stretched state; and a one-piece fastener affixed to said proximal end of said stretchable elongated band, said fastener having an opening comprising a first cavity, said first cavity adapted to accept said distal end of said stretchable elongated band in its stretched state, said first cavity comprising:
a longitudinal channel having a predetermined channel width greater than said predetermined first width and a predetermined channel depth which is less than said predetermined first thickness, said stretchable elongated band being moveable in said longitudinal channel in either longitudinal direction when in its stretched state,
such that said longitudinal channel of said first cavity in said fastener frictionally engages said stretchable elongated band as said stretchable elongated band is returned to its un-stretched state.

2. The friction fit fastening apparatus of claim 1 wherein said predetermined first thickness of said the elongated stretchable band in its un-stretched state is between 1.5 and 2.0 millimeters thick.

3. The friction fit fastening apparatus of claim 1 wherein said predetermined first width of said elongated stretchable strap in its un-stretched state, is between 25 and 30 millimeters.

4. The friction fit fastening apparatus of claim 1 wherein said elongated stretchable band has a stretching coefficient of between 35 and 45 percent.

5. The friction fit fastening apparatus of claim 1, wherein said fastener further comprises a second cavity adapted to accept said proximal end of said stretchable elongated band in its stretched state, said second cavity comprising:
a second longitudinal channel having a predetermined second channel depth which is less than said predetermined first thickness, said second longitudinal channel adapted to accept said stretchable elongated band in its stretched state,
said second cavity in said fastener thereby affixing said proximal end of said stretchable elongated band to said fastener.

6. The friction fit fastening apparatus of claim 1 wherein said first cavity further includes a concave arrangement to facilitate the insertion of the stretchable elongated band in the first cavity.

7. A friction fit fastening apparatus comprising:
a stretchable elongated tube having a proximal end and a distal end, said stretchable elongated tube having a predetermined first circumference in its un-stretched state;
a fastener affixed to said proximal end of said stretchable elongated tube, said fastener having a first cavity adapted to accept said distal end of said stretchable elongated tube in its stretched state, said first cavity comprising:
a channel having a predetermined channel circumference which is less than said predetermined first circumference, said channel adapted to accept said stretchable elongated tube in its stretched state,
such that said channel of said first cavity in said fastener frictionally engages said stretchable elongated tube as said stretchable elongated tube is returned to its un-stretched state; and
a flexible apron affixed to said fastener, said flexible apron adapted to disperse tension exerted by said stretchable elongated tube when said tube is frictionally engaged by said fastener.

8. The friction fit fastening apparatus of claim 7 wherein said elongated stretchable tube is hollow.

9. The friction fit fastening apparatus of claim 7 wherein said elongated stretchable tube is solid.

10. The friction fit fastening apparatus of claim 7 wherein said elongated stretchable tube has an oval cross-sectional shape.

11. A friction fit fastening apparatus comprising:
a stretchable elongated tube having a proximal end and a distal end, said stretchable elongated tube having a predetermined first circumference in its un-stretched state;
a fastener affixed to said proximal end of said stretchable elongated tube, said fastener having a first cavity adapted to accept said distal end of said stretchable elongated tube in its stretched state, said first cavity comprising:
a channel having a predetermined channel circumference which is less than said predetermined first circumference, said channel adapted to accept said stretchable elongated tube in its stretched state,
such that said channel of said first cavity in said fastener frictionally engages said stretchable elongated tube as said stretchable elongated tube is returned to its un-stretched state; and
a rib-shape extension protruding from said fastener and adapted to contact a body part and reduce pinching of said stretchable elongated tube against the body part.

12. The friction fit fastening apparatus of claim 11 wherein said elongated stretchable tube is hollow.

13. The friction fit fastening apparatus of claim 11 wherein said elongated stretchable tube is solid.

14. The friction fit fastening apparatus of claim 11 wherein said elongated stretchable tube has an oval cross-sectional shape.

* * * * *